United States Patent [19]

Maender et al.

[11] 4,187,249

[45] Feb. 5, 1980

[54] PROMOTING THE REACTION OF SODIUM SALTS OF FORMYL DERIVATIVES OF AROMATIC AMINES TO FORM NITRODIARYLAMINES

[75] Inventors: Otto W. Maender, Copley; Gene R. Wilder, Medina, both of Ohio

[73] Assignee: Monsanto Company, St. Louis, Mo.

[21] Appl. No.: 864,195

[22] Filed: Dec. 27, 1977

[51] Int. Cl.$^2$ ............................................. C07C 85/20
[52] U.S. Cl. ..................................... 260/576; 260/571
[58] Field of Search ................................ 260/576, 571

[56] References Cited

FOREIGN PATENT DOCUMENTS 1056619  5/1959  Fed. Rep. of Germany ............ 260/576
1455207  11/1976  United Kingdom ..................... 260/576

OTHER PUBLICATIONS

Rondestvedt, "J. Org. Chem.", 42(10), pp. 1786–1790, (1977).
Sharnin et al., "J. Org. Chem. USSR", 6, pp. 990–992, (1970).

*Primary Examiner*—John Doll
*Attorney, Agent, or Firm*—Gordon B. Seward

[57] ABSTRACT

Promoting the reaction of sodium salts of formyl derivatives of aromatic amines by compounds of potassium, cesium or rubidium to form nitrodiarylamines is disclosed.

7 Claims, No Drawings

PROMOTING THE REACTION OF SODIUM SALTS OF FORMYL DERIVATIVES OF AROMATIC AMINES TO FORM NITRODIARYLAMINES

The invention relates to the preparation of nitrodiarylamines which are valuable intermediates for the preparation of dyestuffs and antidegradants. For example, 4-nitrodiphenylamine is an important intermediate for rubber antidegradants. The invention particularly relates to the preparation of 4-nitrodiphenylamine from p-nitrochlorobenzene.

The Ullmann condensation has been used in several modifications to form diarylamines, all involving reaction of an aryl halide with an aryl amine, one or both of which contains an activating substituent, and usually with a copper catalyst. By utilization of the formyl derivative as an activated form of the aryl amine, and a nitrohalobenzene as an activated form of the aryl halide, the reaction can be effected without the usual copper catalyst, providing there is present a so-called acid acceptor for which purpose potassium carbonate is commonly used. For example, 4-nitrodiphenylamine can be formed by condensing formanilide and p-nitrochlorobenzene with the aid of potassium carbonate. The condensation of sodium formanilide with p-nitrochlorobenzene would appear to offer a possible synthesis route to 4-nitrodiphenylamine and there is an economical incentive to use sodium salts. However, it was found that the sodium salts of the formyl derivatives of aromatic amines are sluggish reactants. High reaction temperatures are required, with adverse affect on product quality and increased tertiary amine formation. Large quantities of polar solvent are required as reaction promoter to effect reasonable reaction rates and yields. An improved method of promoting the reaction has now been found.

In accordance with the present invention, a process of making nitrodiarylamines has been discovered based on reaction of sodium salts which comprises reacting a sodium salt of the formyl derivative of an aromatic amine with a nitrohaloarene containing reactive halogen and a reaction promoting amount of a compound of potassium, cesium or rubidium or mixture thereof effective for promoting the reaction. In such compounds, the anion appears to be largely a matter of choice examples being halogen, carbonate, bicarbonate, sulfate, or acyl such as formate, acetate and benzoate or the anion from the formyl derivative of an aromatic amine. Thus, a portion of the sodium reactant, for example 10 molar percent, may be replaced by the corresponding potassium, cesium or rubidium salt. The combined molar ratio should be about 1.0 to 1.5 moles per mole of nitrohaloarene. Reaction temperatures will usually be within the range of 150°–205° C., preferably 160°–180° C. In other embodiments, the anion of the reaction promoter does not enter into the reaction and the promoter will be added in addition to the molar proportion of sodium salt required for the reaction. In such case, the molar proportion of the sodium salt should be within the range of 1.0 to 1.5 moles per mole of nitrohaloarene and preferably about 1.3 moles. A potassium salt is the preferred promoter. The molar ratio of the promoter is usually 0.025–1.0 mole equivalent and preferably 0.5–0.7 mole equivalent of metal per mole of nitrohaloarene. Only small amounts of polar solvent are needed to observe the aforesaid promoter action.

Using an N-formylaromatic amine as the polar solvent with the sodium salt gives optimum results. For such results, the N-formyl-aromatic amine is desirably used in amount of at least about 0.4 mole per mole of nitrohaloarene. The salt need not be isolated prior to reaction but may be formed in situ in a suitable reaction medium and reacted with nitrohaloarene. However, the quality of the salt is of the utmost importance for good results in reaction with nitrohaloarene. For example, it should be essentially free of bound water and alcohol.

The exclusion of a solvent other than the aforesaid formyl derivative is, in general, desirable. On the other hand, a little inert solvent may serve to control the reaction temperature. Inert non-polar solvents such as xylene, cumene, or diisopropylbenzene may be used. The process is operative with polar solvents such as: 1,2-bis-2-methoxyethoxyethane, dimethyl formamide and dimethylsulfoxide. However, the aforesaid polar solvents are expensive and not entirely inert but subject to loss from reaction involving the solvent as well as loss on recovery, especially at the temperatures for reaction. The formyl derivative corresponding to the sodium salt to be reacted is a precursor for the desired product so that any consumption due to reaction is not loss. Also, the formyl derivatives of aromatic primary amines inhibit further reaction of the desired nitrodiarylamine to tertiary amine by-product as well as being solvents for the sodium salt. The formyl derivative of an aromatic primary amine different from the one used to form the sodium salt may be used if a mixture of nitrodiarylamine products is desired.

Experimental evidence from differential scanning colorimetry indicates that sodium formanilide forms an adduct with formanilide. The formation of such a complex is undoubtedly significant for the reaction of sodium formanilide with p-nitrochlorobenzene. Sodium formanilide is a high melting solid and the formation of a complex with formanilide appears to lower the melting point and increase the reactivity for reasons as yet obscure. When the ratio of formanilide to p-nitrochlorobenzene is 2, the rate of reaction with sodium formanilide is considerably faster than observed for a corresponding ratio of 1.4. The results imply that solvation of the trasition state is extremely important. A non-polar solvent appears to inhibit the rate of solvation of the formanilide-sodium formanilide complex.

In general, for reacting sodium formanilide, formanilide and p-nitrochlorobenzene, it is desirable to use 0.4–2.6 moles of formanilide per mole of p-nitrochlorobenzene, preferred proportions being about 1.3–1.6 moles of formanilide per mole of p-nitrochlorobenzene. The reaction rates and yields from sodium formanilide are excellent when the mole ratio of formanilide to sodium formanilide is equal to or exceeds 1; preferably 1–2, and the mole ratio of formanilide to p-nitrochlorobenzene is equal to or exceeds 1.3. Any inert solvent, if used, should be kept at a minimum, because of the adverse affect on the reaction rate. The high formanilide level almost eliminates the formation of 4,4'-dinitrotriphenylamine but the amount is increased several fold when dimethylformamide replaces formanilide.

If desired, aniline may be added to reduce carbon monoxide evolution and ultimately decrease formic acid usage. It is believed that aniline traps carbon monoxide by transamidation with N-formyl-p-nitrodiphenylamine intermediate. Thus, the reduction of carbon monoxide is accompanied by conversion of aniline to formanilide.

The alkali metal salts of N-formylaromatic amines may be prepared from the corresponding alkali metal alkoxides in dimethylformamide or xylene. The alcohol is constantly removed to drive the reaction to completion. When xylene is used, a suitable solvent for making sodium salts, the solid salt is allowed to separate under stirring. In dimethylformamide, a solution is present throughout and refractometer readings of the distillate are taken periodically until the refractive index of the higher boiling solvent is obtained.

The method selected for making sodium formanilide may influence the quality of the product and determines whether the method is acceptable for commercial use in making 4-nitrodiphenylamine. For example, metallic sodium is troublesome and dangerous to handle, liberates explosive hydrogen and, if used in conjunction with recycled material as would ordinarily be necessary in commercial operation, enters into side reactions with resultant increase in by-products and reduction in yield.

A variety of nitrohaloarenes have been proposed for making nitrodiarylamines, any of which appear to be suitable for use in the process of the invention. Illustrative of such nitrohaloarenes are: o-nitrochlorobenzene, o-nitrobromobenzene, p-nitrochlorobenzene, p-nitrobromobenzene, m-nitrochlorobenzene, m-nitrobromobenzene, 1-chloro-2-methyl-4-nitrobenzene, 1-chloro-3-methyl-4-nitrobenzene, 1-chloro-2-nitronaphthalene, 3,4-dichloronitrobenzene, 3-methyl-4-chloronitrobenzene, 2-methyl-4-chloronitrobenzene, 2-ethyl-4-chloronitrobenzene, 2,3-dimethyl-4-chloronitrobenzene, 2,5-dimethyl-4-chloronitrobenzene, 3,5-dimethyl-4-chloronitrobenzene and p-nitrofluorobenzene.

The process is believed to be a general one for condensation of aromatic primary amines as the aforesaid sodium salts of the formyl derivatives, but has been examined most extensively with formanilides. Formanilides substituted in the benzene nucleus by one or more substituents inert under the reaction conditions, for example, one or more alkyl, alkoxy, nitro, fluoro or chloro substituents, are suitable. Illustrative substituted formanilides which may be used in the process are the sodium salts of: 3-chloroformanilide, 4-chloroformanilide, 2-methylformanilide, 3-methylformanilide, 4-methylformanilide, 3-ethylformanilide, 3,4-dimethylformanilide, 3-methoxyformanilide, 4-methoxyformanilide, 4-ethylformanilide, 4-isopropylformanilide, 4-butylformanilide, 3,4-dichloroformanilide and 4-nitroformanilide.

The reaction may be carried out in mild steel, stainless steel, glass or glass-lined vessels. After the condensation reaches the selected end-point, the alkali metal halide by-product may be removed by water washing; solvent, if present, removed by distillation, and the residue cooled to 5°–10° C., preferably about 5° C. to recover nitrodiarylamine by crystallization.

Potassium formanilide believed to be a new compound may be prepared and isolated as follows: From 122 parts by weight (1.3 mole) of 45% potassium hydroxide, 300 parts by weight of butanol and 100 parts by weight of xylene, 1.3 mole of potassium butoxide is prepared by stripping out water into a suitable water trap. The potassium butoxide is then added to a slurry of 156 parts by weight of formanilide in 250 parts by weight of xylene at ambient temperature. The butanolxylene slurry is distilled in vacuo (100 mm. Hg.) until the overhead refractive index is 1.497, xylene being added to maintain the volume. The slurry is cooled to ambient temperature and the vacuum released under nitrogen. The slurry is then filtered and the xylene replaced by benzene, always keeping a liquid layer over the cake. The benzene is replaced by hexane in the same fashion, the bulk of the hexane is pulled through and the cake quickly transferred to a suitable container and dried. One obtains a crystalline white product soluble in dimethyl formamide, methanol and butanol. Potassium formanilide melts at 184°–186° C. An associated formanilide-K-formanilide adduct melts at 140°–145° C. and some samples of potassium formanilide will show both exotherms in differential scanning calorimetry.

A suitable procedure for preparing sodium formanilide is the following:

To 41.6 grams of formanilide (0.35 mole) dissolved in 200 ml. of xylene is added dropwise under stirring at 80° C. under about 100 mm Hg. pressure 70.2 g. of 25% by weight sodium methoxide in methanol (0.325 mole). The methanol is distilled off followed by the higher boiling solvent in vacuo at a pot temperature below about 85° C. until the refractive index in the distillate is that of xylene (1.497). The solid sodium salt is separated by filtration and protected from moisture until ready for use. To prepared sodium formanilide and formanilide for use without isolating the sodium formanilide the foregoing procedure is followed omitting the filtration step, employing the desired excess of formanilide and replacing the methanol by xylene or other suitable solvent to keep the slurry fluid. The p-nitrochlorobenzene and reaction promoter are then added and xylene stripped out until the desired temperature is reached.

The results suggest that the larger ions of the reaction promoter are exchanging with sodium in the polar solvent medium thereby enhancing the solubility and reactivity of the organic anion. The amount of polar solvent required is merely enough to solvate the sodium salt of the formyl derivative and allow the larger ion to come into the solvated cluster and exchange. The larger ions appear to be more readily solvated, thereby allowing the major proportion of the reaction to proceed primarily via a low concentration of the larger ion intermediate. Because of its lower solubility threshold than KCl, the NaCl precipitate from the sodium formanilide-KCl equilibrium with potassium formanilide and NaCl can act as an additional driving force for shifting the equilibrium in the direction of potassium formanilide. However, the invention is not limited to any theory of the reaction mechanism. Regardless of the explanation, a number of important improvements are achieved by the invention. For example, by use of the promoter in the condensation of p-nitrochlorobenzene and sodium formanilide comparable results can be obtained at lower formanilide solvent levels, and lower reaction temperatures may be employed; higher yields and conversions are obtained for a given formanilide level; lower amounts of by-products form and lighter colored product and mother liquor are produced. The lower formanilide solvent levels reduce the recovery and recycling requirements. As noted, formanilide represses formation of dinitrotriphenylamine exacerbated by use of sodium formanilide as a reactant. Other polar solvents, for example, dimethylformanilide and dimethylsulfoxide do not exert such repression. Also by use of the promoter comparable results can be obtained at higher levels of inert solvent.

DESCRIPTION OF PREFERRED EMBODIMENTS

EXAMPLE 1

Into a suitable reactor is charged 78.5 parts by weight (0.5 mole) of p-nitrochlorobenzene, 93.8 parts by weight (0.65 mole) of sodium formanilide, 96 parts by weight (0.8 mole) of formanilide and 18 parts by weight (0.25 mole) of potassium chloride. The mixture is gradually heated and stired; and, at about 134° C., evolution of carbon monoxide begins. Heating is continued until the temperature reaches 170°, at which temperature the reaction mixture becomes self-heating. Stirring is continued at 170°. After about an hour, 18 parts by weight of carbon monoxide are evolved; and reaction is stopped, xylene added, and the xylene solution washed with 250 parts by weight of water, separated from the water and cooled to 10° C. The crystals of 4-nitrodiphenylamine which form are separated by filtration and washed with a little xylene. From the mother liquor a second crop of 4-nitrodiphenylamine is recovered. The total yield is 105.4 parts by weight, or 98.5% yield. The p-nitrochlorobenzene is reacted completely. Heating similar molecular proportions of materials and a little xylene to help control the temperature at 180° C. in the absence of potassium chloride for 2½ hours gives an 86% yield and 96% conversion. In general, the yields are 90–99% from the foregoing reaction ratios and procedure using potassium chloride and the expected yield in its absence about 10% less. The reactions can be run in a closed system, i.e., an autoclave, but no advantage is achieved.

Results from similar reactions, one of which was run in an autoclave, also employing 1.3 mole of sodium formanilide per mole of p-nitrochlorobenzene are summarized below. The moles of formanilide and KCl are moles per mole of p-nitrochlorobenzene. An inert solvent, xylene, is used in the reactions summarized in the table below, the amount being recorded as parts by weight per mole of p-nitrochlorobenzene.

| Example | 1-A | 1-B | 1-C | 1-D | 1-E |
|---|---|---|---|---|---|
| Formanilide moles | 0.4 | 0.8 | 0.8 | 1.6 | 1.5 |
| KCl moles | 0.7 | 0.7 | 0.2 | 0.5 | 0.5 |
| Xylene, parts by weight | 500 | 500 | 500 | 200 | 200 |
| Temperature, °C. | 25–162[1] | 134–170[2] | 120–168[3] | 140–170[4] | 150–181 |
| Time, hrs. | 5 | 2 | 3 | 3.5 | 1.1 |
| Yield, % | 82.2 | 85.5 | 86.7 | 86.5 | 95.8 |
| Conversion, % | 94.6 | 92.2 | 96 | 89.2 | 100 |

[1]gradually heated from 25° to 162° over the 5-hour period.
[2]heated from 134° to 170° C. over a period of about 50 minutes, then kept at about 128° the rest of the time.
[3]heated from 120° to 170° C. over about an hour then at about 168° for two hours.
[4]run in an autoclave at 150–195 pounds per square inch pressure.

EXAMPLE 2

Into a suitable reactor is charged 64.4 parts by weight (0.45 mole) of sodium formanilide and 8.0 parts by weight (0.05 mole) of potassium formanilide to give a 90/10 ratio of the salts. In addition, there is added 23.4 parts by weight (0.193 mole) of formanilide and 60.6 parts by weight (0.385) of p-nitrochlorobenzene. The mixture is heated and stirred for 1.5 hours at 152°–160° C. The product is isolated as described in Example 1 to obtain 75.1 parts by weight or 93% yield of 4-nitrodiphenylamine. Conversion of p-nitrochlorobenzene is 98.4%.

EXAMPLES 3–7

Preparations of 4-nitrodiphenylamine are carried out by charging to a suitable reactor 0.385 gram molecular proportion of p-nitrochlorobenzene, 0.25 grams molecular proportion of formanilide, 0.5 grams molecular proportion of sodium formanilide and the indicated gram molecular equivalent (m.e.) of a reaction promoter. A little xylene is added to aid in controlling the reaction temperature of the mixture. The reaction mixture is heated at 168°–170° C. until the evolution of carbon monoxide subsides.

The results are summarized below, where Example 3 is a control without promoter.

| Ex. | Promoter | m.e | Hrs. of heating and liters of gas evolved | Yield,% | Conversion of p-Nitrochloro benzene |
|---|---|---|---|---|---|
| 3 | none | — | 1.5/8.8 | 76.9 | 96.8 |
| 4 | CsCl | 0.1 | .75/10.2 | 84.6 | 99.4 |
| 5 | Rb$_2$CO$_3$ | 0.1 | 1.0/10.1 | 83.6 | 99.6 |
| 6 | KOH,85% | 0.1 | 1.5/5.3 | 74.6 | 92.8 |
| 7 | KOH,87.3% | 0.025 | 1.5/7.2 | 77.2 | 94.3 |

Strong alkalis foster side reactions; and it will be noted that 85% KOH in 0.1 molecular equivalent amounts obscures the promoting effect under the conditions described but it is slightly discernible at 0.025 molecular equivalents. In the absence of a promoter the reaction mixtures are olive green and produce a dark mother liquor; but with a potassium salt as promoter the reaction mixtures are orange to deep red and the characteristic color is observed with potassium hydroxide.

EXAMPLES 8–12

Preparations of 4-nitrodiphenylamine are carried out by charging to a suitable reactor 93 parts by weight (0.65 mole) of sodium formanilide, 97 parts by weight (0.8 mole) of formanilide, 50 parts by weight of xylene, 78.5 parts by weight (0.5 mole) of p-nitrochlorobenzene and 0.5 mole equivalent, based on the potassium content, per mole of p-nitrochlorobenzene of a potassium salt. The contents of the reactor are heated at 170°–175° C. for about 1½ hours and the 4-nitrodiphenylamine isolated as described in Example 1. The results are shown in tabular form below:

| Example | Promoter | Yield, % | Conversion of p-nitro-chlorobenzene, % |
|---|---|---|---|
| 8 | potassium acetate | 93.3 | 98.5 |
| 9 | potassium benzoate | 95.1 | 97.5 |
| 10 | potassium sulfate | 90.6 | 98.3 |
| 11 | tri-potassium phosphate | 71.7 | 82.6 |
| 12 | potassium bromide | 93.0 | 97.0 |

The results show strong promoting effect with all the salts except tri-potassium phosphate. Although the promoting effect of the metal may in some instances be obscured by adverse effects of the anion, a simple experiment or two will show whether a given potassium, cesium or rubidium compound is effective for promoting the reaction.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property of privilege is claimed are defined as follows:

1. The process which comprises forming nitrodiarylamine by reacting in the presence of a polar solvent
   (A) the sodium salt of the formyl derivative of an aromatic amine with
   (B) nitrohaloarene containing reactive halogen and
   (C) a reaction promoting amount of a compound of potassium, cesium or rubidium or mixture thereof effective for promoting the reaction.

2. The process which comprises forming nitrodiarylamine by reacting in the presence of a polar solvent
   (A) the sodium salt the anion of which is from formanilide or formanilide substituted in the benzene nucleus by one or more alkyl, alkoxy, fluoro, chloro or nitro substituents with
   (B) nitrohalobenzene in the presence of a reaction promoting amount of (C) an alkali metal salt wherein the alkali metal is potassium, cesium, rubidium, or mixture thereof and the anion is as in A or is halogen, acyl, carbonate, bicarbonate or sulfate.

3. The process of claim 2 wherein (A) is sodium formanilide, (B) is p-nitrochlorobenzene, and (C) is potassium chloride.

4. The process of claim 1 wherein (A) is sodium formanilide, (B) is p-nitrochlorobenzene and (C) is potassium formanilide.

5. The process of claim 4 wherein the polar solvent is formanilide.

6. The process of claim 3 wherein the polar solvent is formanilide.

7. The process which comprises forming 4-nitrodiphenylamine by heating sodium formanilide, p-nitrochlorobenzene, formanilide and a reaction-promoting amount of a potassium salt effective for promoting the reaction, the sodium formanilide being 1.0–1.5 moles and the formanilide 0.4–2.6 moles per mole of p-nitrochlorobenzene.

* * * * *